(12) United States Patent
Piskun

(10) Patent No.: US 7,344,547 B2
(45) Date of Patent: *Mar. 18, 2008

(54) LAPAROSCOPIC INSTRUMENTS AND TROCAR SYSTEMS AND RELATED SURGICAL METHOD

(75) Inventor: Gregory Piskun, Brooklyn, NY (US)

(73) Assignee: Phavel Systems, Inc., Brooklyn, NY (US)

( * ) Notice: Subject to any disclaimer, the term of this patent is extended or adjusted under 35 U.S.C. 154(b) by 644 days.

This patent is subject to a terminal disclaimer.

(21) Appl. No.: 10/253,244

(22) Filed: Sep. 24, 2002

(65) Prior Publication Data

US 2003/0028179 A1   Feb. 6, 2003

Related U.S. Application Data

(63) Continuation-in-part of application No. 09/397,630, filed on Sep. 15, 1999, now Pat. No. 6,454,783.

(60) Provisional application No. 60/100,823, filed on Sep. 15, 1998.

(51) Int. Cl.
*A61B 17/34* (2006.01)

(52) U.S. Cl. .................................................. 606/185

(58) Field of Classification Search ................ 606/185, 606/186, 1, 144; 604/164.03, 174
See application file for complete search history.

(56) References Cited

U.S. PATENT DOCUMENTS

| | | |
|---|---|---|
| 2,669,991 A | 2/1954 | Curutchet |
| 4,644,951 A | 2/1987 | Bays |
| 4,863,430 A | 9/1989 | Klyce et al. |
| 5,241,968 A | 9/1993 | Slater |
| 5,242,409 A | 9/1993 | Buelna |
| 5,269,772 A * | 12/1993 | Wilk .......................... 604/284 |
| 5,312,391 A * | 5/1994 | Wilk ............................. 606/1 |
| 5,330,486 A | 7/1994 | Wilk |
| 5,366,478 A * | 11/1994 | Brinkerhoff et al. ......... 606/213 |
| 5,391,156 A * | 2/1995 | Hildwein et al. ........... 604/174 |
| 5,395,367 A | 3/1995 | Wilk |
| 5,480,410 A * | 1/1996 | Cuschieri et al. ........... 606/213 |
| 5,549,563 A | 8/1996 | Kronner |
| 5,549,637 A | 8/1996 | Crainich |
| 5,571,115 A | 11/1996 | Nicholas |

(Continued)

FOREIGN PATENT DOCUMENTS

WO    WO97/42889    * 11/1997

*Primary Examiner*—Anhtuan T. Nguyen
*Assistant Examiner*—Tuan V. Nguyen
(74) *Attorney, Agent, or Firm*—R. Neil Sudol; Henry D. Coleman; William J. Sapone

(57) ABSTRACT

Laparoscopic instruments and trocars are provided for performing laparoscopic procedures entirely through the umbilicus. A generally C-shaped trocar provides increased work space between the hands of the surgeon as well as S-shaped laparoscopic instruments placed through the trocar when laparoscopic instrument—trocar units are placed through the umbilicus. In order to facilitate retraction of intra-abdominal structures during a laparoscopic procedure, an angulated needle and thread with either one-or two sharp ends is provided. Alternatively, an inflatable unit having at least one generally C-shaped trocar incorporated within the unit's walls can be placed through the umbilicus following a single incision. Generally S-shaped laparoscopic instruments may be placed through the generally C-shaped trocars to facilitate access to intra-abdominal structures.

22 Claims, 4 Drawing Sheets

U.S. PATENT DOCUMENTS

| | | |
|---|---|---|
| 5,571,137 A | 11/1996 | Marlow et al. |
| 5,575,799 A | 11/1996 | Bolanos et al. |
| 5,578,048 A | 11/1996 | Pasqualucci et al. |
| 5,634,911 A * | 6/1997 | Hermann et al. ............ 604/256 |
| 5,672,168 A | 9/1997 | de la Torre et al. |
| 5,725,536 A | 3/1998 | Oberlin et al. |
| 5,782,859 A | 7/1998 | Nicholas et al. |
| 5,860,995 A | 1/1999 | Berkelaar |
| 5,931,832 A | 8/1999 | Jensen |
| 5,964,781 A | 10/1999 | Mollenauer et al. |
| 5,997,515 A * | 12/1999 | de la Torre et al. ......... 604/256 |
| 6,033,426 A * | 3/2000 | Kaji ............................ 606/213 |
| 6,077,288 A * | 6/2000 | Shimomura et al. ......... 606/185 |
| 6,099,506 A * | 8/2000 | Macoviak et al. ........... 604/173 |
| 6,217,590 B1 | 4/2001 | Levinson |
| 6,551,270 B1 | 4/2003 | Bimbo et al. |
| 2003/0036748 A1 | 2/2003 | Cooper et al. |

* cited by examiner

LAPAROSCOPIC INSTRUMENTS AND TROCAR SYSTEMS AND RELATED SURGICAL METHOD

CROSS-REFERENCE TO RELATED APPLICATION

This application is a continuation in part of application Ser. No. 09/397,630, filed Sep. 15, 1999, now U.S. Pat. No. 6,454,783, which, in turn, claims the benefit of Provisional Application No. 60/100,823, filed Sep. 15, 1998.

FIELD OF THE INVENTION

The present invention relates to surgical instruments, and particularly to laparoscopic instruments, which facilitate the performance of laparoscopic procedures entirely through the umbilicus.

BACKGROUND INFORMATION

Abdominal laparoscopic surgery gained popularity in the late 1980's, when benefits of laparoscopic removal of the gallbladder over traditional (open) operation became evident. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall.

Laparoscopic procedures generally involve insufflation of the abdominal cavity with CO2 gas to a pressure of around 15 mm Hg. The abdominal wall is pierced and a 5-10 mm in diameter straight tubular cannula or trocar sleeve is then inserted into the abdominal cavity. A laparoscopic telescope connected to an operating room monitor is used to visualize the operative field, and is placed through (one of) the trocar sleeve(s). Laparoscopic instruments (graspers, dissectors, scissors, retractors, etc.) are placed through two or more additional trocar sleeves for the manipulations by the surgeon and surgical assistant(s).

Recently, so-called "mini-laparoscopy" has been introduced utilizing 2-3 mm diameter straight trocar sleeves and laparoscopic instruments. When successful, mini-laparoscopy allows further reduction of abdominal wall trauma and improved cosmesis. However, instruments used for mini-laparoscopic procedures are generally more expensive and fragile. Because of their performance limitations, due to their smaller diameter (weak suction-irrigation system, poor durability, decreased video quality), mini-laparoscopic instruments can generally be used only on selected patients with favorable anatomy (thin cavity wall, few adhesions, minimal inflammation, etc.). These patients represent a small percentage of patients requiring laparoscopic procedure. In addition, smaller, 2-3 mm, incisions may still cause undesirable cosmetic outcomes and wound complications (bleeding, infection, pain, keloid formation, etc.).

Since the benefits of smaller and fewer body cavity incisions are proven, it would be attractive to perform an operation utilizing only a single incision in the navel. An umbilicus is the thinnest and least vascularized, and a well-hidden, area of the abdominal wall. The umbilicus is generally a preferred choice of abdominal cavity entry in laparoscopic procedures. An umbilical incision can be easily enlarged (in order to eviscerate a larger specimen) without significantly compromising cosmesis and without increasing the chances of wound complications. The placement of two or more standard (straight) cannulas and laparoscopic instruments in the umbilicus, next to each other, creates a so-called "chopstick" effect, which describes interference between the surgeon's hands, between the surgeon's hands and the instruments, and between the instruments. This interference greatly reduces the surgeon's ability to perform a described procedure.

Thus, there is a need for instruments and trocar systems, which allow laparoscopic procedures to be performed entirely through the umbilicus while at the same time reducing or eliminating the "chopstick effect". A laparoscopic procedure performed entirely through the umbilicus, using the laparoscopic instruments and trocar system according to an embodiment of the present invention, allows one to accomplish the necessary diagnostic and therapeutic tasks while further minimizing abdominal wall trauma and improving cosmesis.

SUMMARY OF THE INVENTION

The present invention provides laparoscopic instruments and trocar sleeves for the performance of laparoscopic procedures, for instance, entirely through the umbilicus.

An object of the present invention is to provide a laparoscopic instrument-trocar unit, which markedly increases the workspace between the hands of the surgeon when the laparoscopic instrument-trocar units are placed through the umbilicus.

An additional object of the present invention is to provide a generally C-shaped trocar sleeve or laparoscopic cannula, which facilitates reduction in the interference between manipulated laparoscopic instruments.

Another object of the present invention is to provide generally S-shaped laparoscopic instruments, where the proximal curve of "S" corresponds to the "C" curve of the C-shaped trocar sleeve or cannula creating separation between manually controlled ends of the laparoscopic instruments, while the distal curve of the "S" creates a markedly increased work space between laparoscopic instruments.

Another object of the present invention is to provide a stretchable and inflatable generally C-shaped trocar sleeve or cannula for accommodation of the rigid generally S-shaped laparoscopic instruments, which, when inflated creates a single unit with an S-shaped instrument.

Another object of the present invention is to provide an inflatable unit with at least one generally C-shaped trocar sleeve or cannula incorporated within the unit's walls, which can be placed through the umbilicus following a single incision.

Another object of the invention is to provide an angulated needle with two sharp ends and a thread attached to the angle of the needle for use in organ retraction, which allows penetration of the abdominal wall, an intra-abdominal structure, and then the abdominal wall again without a change in the orientation of the needle.

A further object of the present invention is to provide an angulated needle having a long segment on one side of the angle, which terminates in a sharp point and a shorter segment on the other side of the angle, which has a thread, attached to it.

A surgical assembly includes, in accordance with the present invention, a trocar sleeve or cannula and an elongate instrument having at least one preformed inherently C-shaped section. The trocar sleeve or cannula is flexible, while the C-shaped section of the elongate instrument is sufficiently rigid so that the trocar sleeve or cannula bends to conform to the shape of the C-shaped section upon an insertion of the elongate instrument through the trocar sleeve or cannula so that the C-shaped section at least partially traverses the same.

The C-shaped section may be one of two C-shaped sections of the instrument, both of the C-shaped sections being preformed. Where the two C-shaped sections are disposed in a common plane, face in opposing directions and are at least substantially contiguous with one another, the instrument has an S-shaped form. Both C-shaped sections may be substantially rigid. Alternatively, one of the C-shaped sections may the flexible while the other is substantially rigid.

A cannula assembly in accordance with the present invention comprises a plurality of cannulas and a cannula holder. The cannula holder in turn comprises an upper surface, a lower surface disposed below the upper surface, and an outer wall connected between the upper surface and the lower surface. A chamber is enclosed within the upper surface, the lower surface and the outer wall. The cannulas are disposed through the upper surface and the lower surface of the holder. At least one of the cannulas is a flexible cannula or an arcuate cannula that is concave on one outer side and convex on an opposite outer side.

Pursuant to additional features of the present invention, at least a given one of the cannulas is spaced from the outer wall and is coupled to the outer wall of the cannula holder via a connector such as a tubular member parallel to the outer wall of the holder.

Preferably, the cannula holder is an inflatable unit. Alternatively, the cannula holder is substantially rigid or semi-rigid.

Optionally, at least one of the cannulas is disposed within the outer wall of the cannula holder. As a group, the cannulas may have various combinations of shapes and degrees of rigidity. For instance, one or more of the cannulas may be straight and rigid, or curved and rigid, while other cannulas may be straight in a relaxed or nonstressed configuration and flexible so as to bend into a curved configuration upon insertion of an instrument having a curved section with a higher degree of rigidity.

The holder may be formed with at least one passageway extending from the upper surface to the lower surface for the reception of one of the elongate instruments. The passageway communicates with the ambient environment and is accordingly disposed outside of the chamber in the cannula holder. The passageway is preferably, but not necessarily, defined by a flexible cylindrical web so that the passageway is closed upon inflation of the cannula holder. During insertion of a cannula into the passageway, the cannula presses the web apart and forms a gas-tight seal therewith.

The cannula holder may have pre-attached cannulas or be free of attached cannulas but have several air-tight openings (passageways), which can accommodate as many different cannulas as needed during a laparoscopic procedure.

An additional cannula may be disposed outside of the holder chamber and spaced from the holder outer wall, the additional connector being connected to the cannula holder A surgical method comprises, in accordance with a particular embodiment of the present invention, forming an opening in a patient, inserting a deflated or collapsed cannula holder through the opening, thereafter inflating the holder to an at least partially expanded configuration so that the holder seals the opening, and disposing a plurality of cannulas in the holder so that after inflating of the holder the cannulas traverse the holder and extend from outside the patient to inside the patient. After inflating of the holder, a plurality of elongate medical instruments are inserted through respective ones of the cannulas.

Where the holder includes at least one passageway extending from an upper surface of the holder to a lower surface thereof, the disposing of the cannulas in the holder includes passing one of the cannulas through the passageway. The passing of the one cannula through the passageway in the holder is preferably, but not necessarily performed after the inflating of the holder.

The inflating of the holder may be implemented by feeding a fluid such as a saline solution or carbon dioxide gas through a one-way valve into the holder.

The disposing of the cannulas in the holder generally includes coupling at least one of the cannulas to the holder after the inflating of the holder. Alternatively or additionally, at least one of the cannulas is coupled to the holder prior to the inserting of the deflated or collapsed holder through the opening in the patient. In any event, the coupling may be accomplished by inserting the one cannula through a passageway in the holder. The passageway is preferably formed with flexible walls for sealing purposes. Alterntaively, the passageway may be rigid and provided with one or more valve exemplarily in the form of a perforated resin web, which after insertion of laparoscopic instrument will prevent leakage of gas.

Where the cannula holder is substantially rigid or semi-rigid, the surgical method in accordance with the present invention, comprises forming an opening in a patient, inserting the cannula holder through the opening, and disposing a plurality of cannulas in the holder so that after inserting of the holder the cannulas traverse the holder and extend from outside the patient to inside the patient. After inserting of the holder, a plurality of elongate medical instruments are inserted through respective ones of the cannulas.

Pursuant to another feature of the present invention, an instrument and the respective cannula have a C-shaped curve in a region traversing the holder after insertion of that instrument through the respective cannulas.

A laparoscopic medical instrument in accordance with the present invention comprises an elongate shaft having an operative tip at one and a manual actuator at an opposite end, with the shaft having a preformed inherently S-shaped configuration. The shaft may be substantially rigid through or, alternatively, semi-rigid and flexible so that the shaft may be deformed from the S-shaped configuration to a straightened configuration upon application of deformation forces to the shaft. In the latter case, the shaft is made of a material with a memory so that the shaft automatically returns to the S-shaped configuration after relaxation of deformation forces. In another alternative design, the shaft has a first curved C-shaped portion that is resilient and another curved C-shaped portion that is rigid.

In another alternative design of a laparoscopic medical instrument in accordance with the present invention, the shaft has a proximal rigid C-shaped portion and a distal flexible portion. The distal portion is flexed into substantially rigid C-shape by a mechanism, controlled by a manual actuator, so the instrument assumes a rigid S-form when needed by the surgeon.

According to an exemplary embodiment of the present invention, laparoscopic instruments and trocar sleeves or cannulas are provided for performing laparoscopic procedures entirely through the umbilicus. S-shape laparoscopic instruments, which are inserted into the generally C-shaped or flexible cannulas markedly increase the work space between the surgeon's hands as well as the manipulated laparoscopic instruments, particularly when the laparoscopic instrument-trocar units are placed through the umbilicus. In order to facilitate retraction of intra-abdominal structures during a laparoscopic procedure, an angulated needle and thread with either one or two sharp ends is provided. Alternatively, an inflatable or substantially rigid unit having at least one generally C-shaped trocar sleeve or cannula incorporated within the unit's walls can be placed through the umbilicus following a single incision.

DETAILED DESCRIPTION

Figure 1:
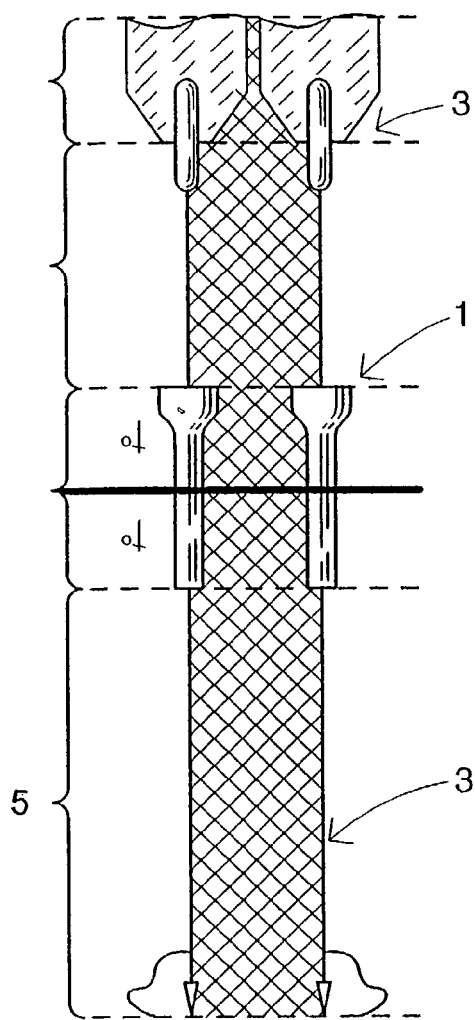
FIG. 1 is a schematic view of a conventional laparoscopic instrument inserted through a conventional straight trocar sleeve or cannula.

The present invention provides laparoscopic instruments and trocar sleeves or cannulas for the performance of laparoscopic procedures entirely through the umbilicus. Referring now in specific detail to the drawings, in which like reference numerals identify similar or identical elements, there is shown in FIG. 1 a conventional, prior art laparoscopic instrument—trocar assembly.

As illustrated in FIG. 1, a conventional trocar sleeve or cannula 1 is an essentially straight, hollow instrument, which allows conventional laparoscopic instruments 3 such as an endoscope of suitable diameter to be inserted through the conventional cannula 1 and into the abdominal cavity 5 of a patient. Conventional cannulas 1 have a diameter of a round 2-15 mm. Once the conventional laparoscopic instruments 3 are in place, standard laparoscopic procedures may be performed, such as cholecystectomy, appendectomy, or simple diagnostic laparoscopy.

As shown in FIG. 1, when conventional trocar sleeves or cannulas 1 and conventional laparoscopic instruments 3 are inserted only through the umbilicus of the patient, the close proximity of the instruments to each other results in the so-called chopstick effect, which is a significant limitation to the manipulation of conventional laparoscopic instruments 3 through conventional trocars 1.

Figure 2A:
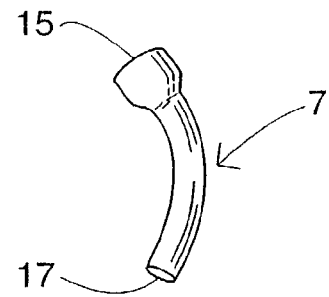
FIG. 2A is a side view and FIG. 2B is an end view of an exemplary embodiment of a flexible C-shaped trocar sleeve or cannula.
Figure 2B:

As shown in FIG. 2A and FIG. 2B, an exemplary C-shaped trocar sleeve or cannula 7 according to an embodiment of the present invention is generally an elongated tube having a proximal end 15 and a distal end 17. In one exemplary embodiment the C-shape curve through ends 15, 17 is bent so that each end portion forms an angle of approximately 30° with respect to a tangent to the center of the trocar sleeve or cannula 7. However, any angle, which sufficiently reduces the chopstick effect, may be used. Thus, exemplary embodiments of the present invention with angles from 5-45° may be used. A C-shaped trocar sleeve or cannula 7 may be made of conventional material as is known in the art. The interior diameter of a C-shaped cannula 7 is preferably around 5 mm. However, in alternate embodiments the interior diameter of the C-shaped cannula 7 may range from 2-15 mm. In one exemplary embodiment, the C-shape is relatively fixed and does not vary, for example when the cannula 7 has a rigid composition. In an alternate exemplary embodiment, the C-shaped cannula 7 is more flexible allowing the surgeon or surgical assistant to bend the cannula 7 changing the angle of the C-shape, for example, via insertion of an instrument into the cannula.

In an alternative design, trocar sleeve or cannula 7 is made of a flexible material with a memory. Trocar sleeve 7 or cannula 7 may have a straight or linear cylindrical configuration in a relaxed state, i.e., in the absence of externally applied forces. Sleeve or cannula 7 assumes the curved or arcuate configuration shown in FIG. 2A upon the insertion through the cannula of a laparoscopic instrument shaft with a curved or arcuate section of sufficiently greater rigidity than the cannula. Cannula 7 then bends through the application of external forces to take the arcuate form shown in FIG. 2A.

Figure 2C:
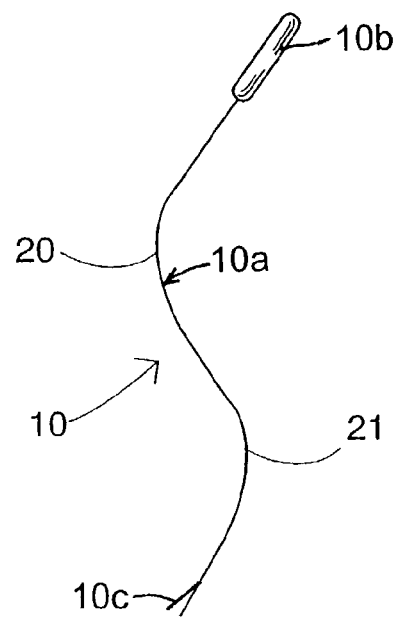
FIG. 2C is an exemplary embodiment of an S-shaped instrument.

FIG. 2C illustrates an exemplary S-shaped laparoscopic instrument 10 in accordance with an embodiment of the present invention. The S-shaped laparoscopic instrument 10 has, for example, a shaft 10a with a preformed inherently S-shaped configuration including a proximal curve 20 and a distal curve 21. Examples of laparoscopic instruments 10 which can be formed generally into an S-shape according to an embodiment of the present invention include but are not limited to scissors, clamps, dissectors, staplers, clip appliers, retrieval bags, and electrocautery instruments. Instruments 10 include a manual actuator 10b at a proximal end and an operative tip 10c at a distal end. The S-shaped shaft 10a may be substantially rigid throughout. Alternatively, shaft 10a or a portion thereof, for example, distal curve 21, may be semi-rigid and flexible so that the shaft may be deformed from the S-shaped configuration to an at least partially straightened configuration upon application of deformation forces to the shaft. In the latter case, the shaft is made of a material with a memory so that the shaft automatically returns to the S-shaped configuration after relaxation of deformation forces. In another alternative, proximal shaft portion 20 is rigid while distal shaft portio n21 is flexible. Distal portion 21 is flexed into substantially rigid C-shape by a locking mechanism (not separately shown), controlled by actuator 10b, so the instrument assumes a rigid S-form when needed by the surgeon. In any event, the S-shape for these instruments can be achieved, for example, by using conventional manufacturing techniques modified to accommodate the S-shape contour of the instrument.

Figure 3:
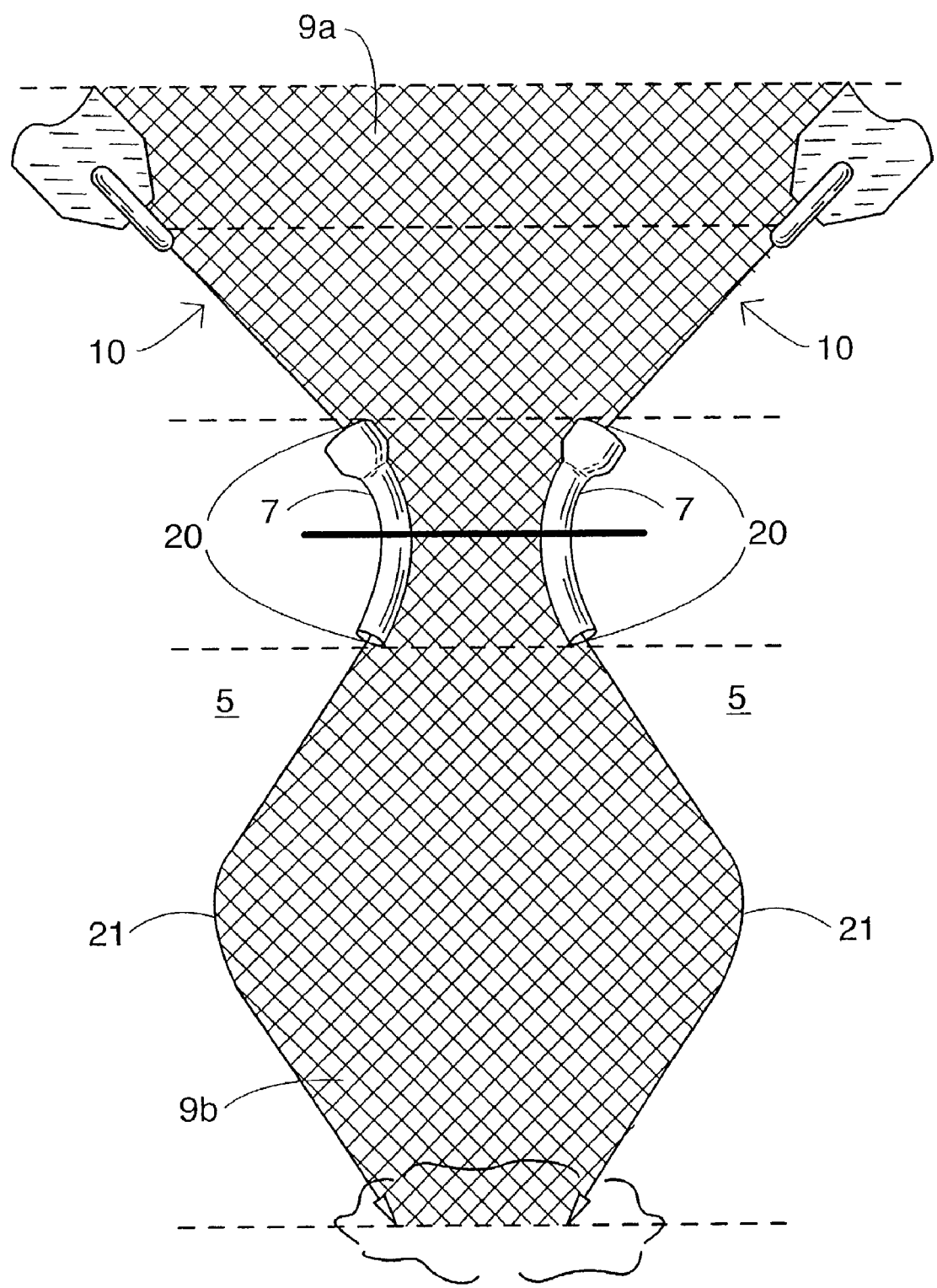
FIG. 3 is a schematic view of an exemplary embodiment of an S-shaped laparoscopic instrument inserted through a C-shaped flexible trocar sleeve or cannula.

As illustrated in FIG. 3, a generally S-shaped laparoscopic instrument 10 may be inserted through a C-shaped trocar sleeve or cannula 7. For example, the proximal curve 20 of the S-shaped instrument 10 corresponds to the curve of the C-shaped cannula 7. The distal curve 21 of the S-shaped instrument 10 also corresponds to the curve of the C-shaped cannula 7 and when inserted through the. Cshaped cannula 7 will be, for example, entirely within the abdominal cavity 5 of the patient. An embodiment of the present invention, for example, a C-shaped cannula 7 and S-shaped laparoscopic instrument 10 allows the surgeon to perform the laparoscopic procedure without making incisions outside of the umbilicus. In accordance with the present invention, the size and curvature of a C-shaped cannula 7 will correspond to the size and curvature of an S-shaped instrument 10 and can include any desired size.

This arrangement of C-shaped cannula 7 and S-shaped instrument 10 eliminates the "chopstick effect" which results from the insertion of conventional laparoscopic instruments 3 through the umbilicus. For example, the proximal curves of the S-shaped instruments 10 and the C-shaped cannula 7 allows the surgeon's hands and the proximal portions of the instruments 20, including the instruments' handles, to be placed as far apart as is convenient for the surgeon. For example, workspace 9a is created. Movement of the proximal portion of one instrument 20 away from the proximal portion 20 of the other also markedly separates the exposed (e.g. outside the body cavity) shafts of each instrument. The distal curve of the S-shaped instrument 21 creates workspace 9b between the portions of the instruments in the abdominal cavity and redirects the distal end of the laparoscopic instrument 10 back toward a target site 8, such as an abdominal organ or other abdominal structure or site.

Thus, an S-shaped laparoscopic instrument 10 may be thought of as having four segments or sections to allow an abdominal procedure to be performed entirely through the umbilicus and yet overcome the "chopstick effect" encountered with conventional laparoscopic: instruments 3 and cannulas 1. First, the portion outside of the patient's abdominal cavity 5 allows sufficient space between the surgeon's hands when manipulating the proximal portion of the laparoscopic instruments 10. Second, the portion at or near the umbilicus, which allows a laparoscopic instrument 10 to enter the abdominal cavity 5 is in close proximity to one or more additional laparoscopic instruments 10 so that all instruments 10 enter the abdomen through the umbilicus. Third, the portion beyond the second portion, which creates separation between laparoscopic, instruments 10 within the abdominal cavity 5. Fourth, the distal end of a laparoscopic instrument 10 is shaped to point back toward the target abdominal organ, tissue, or other site.

Examples of procedures which can be facilitated by the use of C-shaped trocar sleeves or cannulas 7 and S-shaped laparoscopic instruments 10 include, but are not limited to diagnostic laparoscopy, cholecystectomy, appendectomy, ovaro-hysterectomy, removal of a section of bowel, a variety of gastric procedures, biopsy of various abdominal organs including the liver, laparoscopic staging for cancer, and hernia repair.

The following discussion describes, as an example, a cholecystectomy procedure according to an embodiment of the present invention as described in FIGS. 2A-C and FIG. 3. It should be noted, however, that many other laparoscopic procedures may be performed using various embodiments of applicant's invention. The following description, therefore, is merely illustrative and is not intended to limit the present invention to the description given in this example.

A laparoscopic procedure, such as a cholecystectomy, using a curved C-shaped flexible or rigid trocar sleeve or cannula 7 and S-shaped laparoscopic instruments 10 of the present invention is performed with the patient under general anesthesia. Carbon dioxide gas is insufflated intra-abdominally to 15 mm Hg through a 5 mm lateral umbilical incision using, for example, a VERESS™ needle. For example, two curved C-shaped 5 mm cannulas 7 are then inserted through an incision in the umbilicus. The surgeon operates, for example, a 5 mm endoscope with one hand and a 5 mm S-shaped laparoscopic instrument 10 with the other, each of which are passed through a respective cannula 7. The cannula for the endoscope could be straight so that a conventional straight endoscope could be used, the other curved cannula 7 providing separation between the instruments and the surgeon's hands. Pericholecystic adhesions, if present, are removed by blunt or sharp dissection using an S-shaped dissector to expose the dome of the gallbladder. A 2-0 nylon (or other suitable material) stay suture on a needle is placed through the abdominal wall immediately below the right costal margin at the right anterior axillary line, allowing for superior retraction of the gall bladder dome. The removal of the adhesions from around the gallbladder infundibulum is then continued as necessary. A second stay suture is placed through the right flank and then through the neck of the gallbladder allowing for lateral retraction to expose the cystic structures. The cystic duct and cystic artery are dissected, then ligated with clips, utilizing a 5 mm S-shaped clip applier, and then finally transected with an S-shaped scissors. With continued retraction from stay sutures, the gallbladder is removed from the liver bed utilizing an S-shaped electrocautery device equipped with a hook, dissecting the gallbladder from medial to lateral and inferior to superior direction. The perihepatic area is then irrigated using an S-shaped irrigation/suction device.

The above-described procedure is greatly facilitated by the use of S-shaped laparoscopic instruments 10 and C-shaped cannulas 7, allowing the procedure to be performed entirely through the umbilicus while at the same time reducing or eliminating the "chopstick effect". For example, each of the S-shaped laparoscopic instruments is inserted and removed from the active curved cannula 7 as needed during the procedure and conflict with the endoscope is avoided. Thus, as a result, improved cosmesis, reduced operative and post-operative complications, and a less complicated surgical technique are achieved.

Figure 4A:
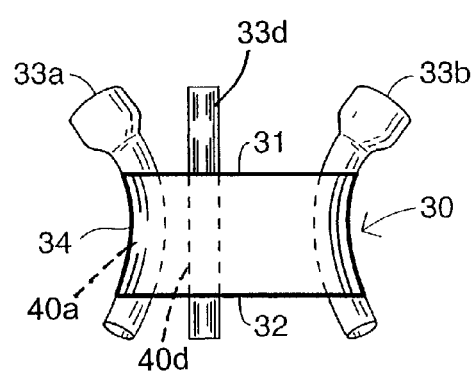
FIG. 4A is a lateral view and FIG. 4B is a perspective view of an exemplary inflatable unit with multiple C-shaped trocar sleeve or cannulas incorporated within the unit.
Figure 4B:
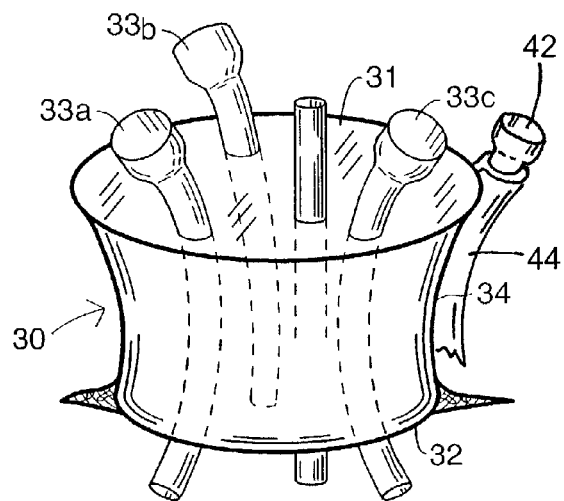

FIG. 4A and FIG. 4B illustrate an inflatable cannula holder 30 having, for example, multiple C-shaped trocar sleeves or cannulas incorporated within the unit 30. The lateral or perimetric outer wall 34 of the inflatable cannula holder unit 30 may vary from extremely flexible and stretchable when deflated, thus facilitating insertion into the umbilical incision, to somewhat rigid when inflated during the surgical procedure. The inflatable unit 30 has, for example, a horizontal upper plate 31 and a horizontal lower plate 32. Curved or arcuate trocar sleeves or cannulas 33a, 33b, and 33c will extend through the horizontal upper plate 31 and horizontal lower plate 32 and may be incorporated within the lateral or perimetric outer wall 34. Cannulas 33a, 33b, 33c may be rigid or flexible members. Cannulas 33a, 33b, and 33c are spaced from one another at the upper plate 31 and the lower plate 32 and concomitantly in a plane of an incision of opening in a patient. One or more straight trocar sleeves or cannulas 33d may also be provided which traverse holder unit 30 and particularly upper surface 31 and lower surface 32 thereof. Any given straight cannula 33d may be rigid or flexible. In the latter case, the cannula 33d may be sufficiently flexible to bend in conformation to a generally C-shaped section 20 or 21 (FIG. 2C) of laparoscopic instrument 10. Shaft 10a or section 20, 21 thereof is either rigid or has a sufficient rigidity to force the bending of cannula 33d. One of more of cannulas 33a, 33b, and 33c may similarly be flexible members with a memory tending to return the cannulas to a straight or arcuate configuration.

Rigid sections may be inserted or attached around the periphery of the horizontal upper 31 or lower 32 plate to add stability. The horizontal upper plate 31 and horizontal lower plate 32 may be, for example concave or straight. At least one and possibly two or more C-shaped trocar sleeves or cannulas 33a, 33b, 33c, (described previously) can be incorporated within the lateral wall 34 of the inflatable unit 30 and are distributed, for example, evenly around the wall 34 of the unit 30. The upper 31 and lower plate 32 are preferably made of a flexible plastic material or other suitable surgical quality material.

In an alternate embodiment, the inflatable unit 30 has one or more C-shaped trocar sleeves or cannulas 7 incorporated within its lateral wall 34, and one or more straight cannula 1, also incorporated within the inflatable unit's lateral wall 34. The straight cannula may accommodate, for example, a straight endoscopic or laparoscopic instrument, while the C-shaped cannulas 7 can accommodate an S-shaped instrument 10 as described above. Thus, even where one of the instruments is relatively straight and passes through a relatively straight cannula 1, the chopstick effect is still reduced as a result of the remaining C-shaped cannulas 7 and S-shaped instruments 10, which provide space between the surgeons hands, the proximal portions of laparoscopic instruments (which includes the straight laparoscope), and the distal ends of the laparoscopic instruments (which also includes the straight laparoscope).

Inflatable unit 30 may include one or more passageways 40a and 40d formed by generally cylindrical webs of resilient material (not separately designated) connected at opposite ends to upper surface 31 and lower surface 32. Upon inflation of unit 30, the webs close the passageways and, upon insertion of respective cannulas 33a and 33d, form a sealed engagement therewith. In one possible mode of use, cannulas 33a and 33d are inserted through passageways 40a and 40d only after placement of unit 30 in an opening formed in a patient and upon inflation of the unit. Alternatively, all cannulas 33a, 33b, 33c, 33d may be disposed within and coupled to unit 30 prior to the positioning thereof in the patient.

The surgeon may place the inflatable unit 30 through an approximately 1.5 to 2.5 cm incision or opening in an external skin surface of the patient at the umbilicus. The unit 30 is inserted prior to inflation with the C-shaped cannulas 33a, 33b, 33c, for example, parallel and in close proximity to each other. The upper plate 31 will remain outside of the umbilicus while the lower plate 32 is located just inside the abdominal cavity 5. Once the unit 30 is properly positioned in the incision or opening, the surgeon or assistant may inflate the unit 30. The unit 30 may be inflated via, for example, a one-directional valve using a syringe or gas line inserted into a narrow hollow tube connected to the unit 30 as is known in the art. The syringe or gas line may be alternatively inserted directly into a one-directional valve. Thus, means for inflating the unit 30 can be similar to the means for inflating a conventional endotracheal tube. Upon inflation, the cannula unit 30 traverses the incision or opening in the patient's skin surface at the umbilicus.

In an exemplary embodiment, the diameter of the inflatable unit 30 increases upon inflation. The unit may be inflated to the extent needed for the particular laparoscopic procedure. By placing the trocar sleeves or cannulas in the lateral walls of the inflatable unit, the surgeon may position a trocar sleeves or cannula, and thus an instrument inserted through a cannula, as far away from the other cannulas and instruments as possible within the confines of a chosen space such as the umbilicus. In addition, the surgeon may change the position of the cannulas and instruments within the umbilicus by rotating the inflatable unit 30 around its vertical axis. This change of position of the cannulas; allows intra-operative adjustments of the position of an instrument as well as the type of instrument to further facilitate the intra-abdominal procedure. Moreover, the inflatable unit 30 seals the opening of the patient's abdominal cavity 5 to prevent leakage of $CO_2$ as a result of the inflation.

An additional cannula 42 may be disposed outside of the holder 30 and spaced from holder outer wall 34. A connector 44 in the form of a web or tube couples cannula 42 to cannula holder 30.

Figure 8:
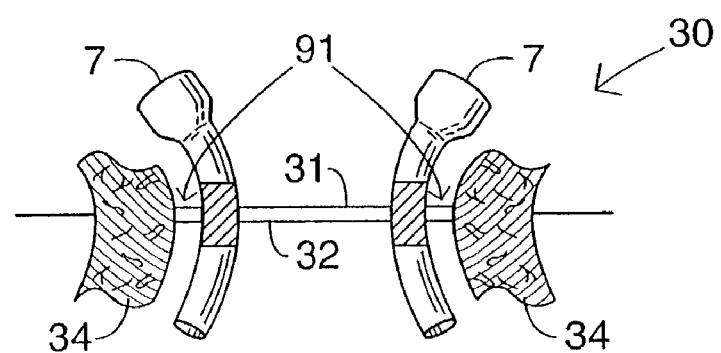
FIG. 8 is a cross-sectional view of an exemplary embodiment of an inflatable unit having multiple cannulas incorporated within the unit.

In an alternate embodiment as shown in FIG. 8, the distance between the upper plate 31 and the lower plate 32 may be reduced, thereby increasing the ability of the trocar sleeve or cannula 7 to move in relation to the wall of the inflatable unit 30. In addition, reducing the distance between the upper plate 31 and lower plate 32 allows the size of the trocar sleeves or cannulas incorporated within the unit 30 to be reduced, which further enhances the ability of the cannula to move in relation to the wall of the inflatable unit 30. In one exemplary embodiment, the cannula is immediately adjacent to the lateral wall 34. In another exemplary embodiment the cannula is not immediately adjacent to the lateral wall 34, but is separated by an additional connector 91 to provide even greater flexibility.

Thus, as an example, the cholecystectomy procedure described above may be performed using the inflatable unit 30 in conjunction with S-shaped laparoscopic instruments 10, rather than using separate cannula/instrument arrangements. Once the gallbladder is transected and removed from the liver bed, it is removed through the 1.5 to 2.5 mm incision along with the inflatable unit 30. If necessary, the initial incision can be extended to remove an enlarged gallbladder. Alternatively, the gallbladder may be opened to remove or crush material present in the gallbladder such as gallstones, facilitating removal of the gallbladder and the inflatable unit 30 through the umbilical incision.

Figure 5A:
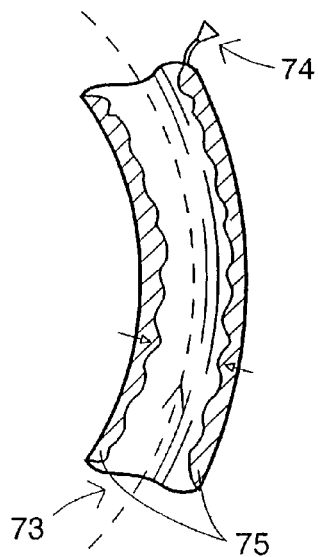
FIG. 5A is a non-inflated lateral view and FIG. 5B is an inflated lateral view of an exemplary inflatable C-shaped trocar sleeve or cannula having a balloon-like structure within the hollow body of the cannula.
Figure 5B:
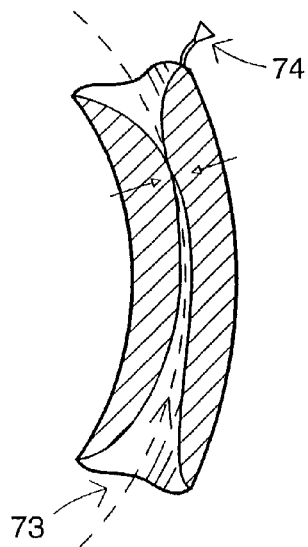

As shown in FIG. 5A and FIG. 5B, an alternate exemplary embodiment of the present invention provides an inflatable unit 70 including a single C-shaped trocar sleeve or cannula 7 having a radially expandable and inflatable balloon-like structure 75 incorporated within the hollow lumen 73 of the cannula. A single laparoscopic instrument may be inserted within this inflatable unit 70. This unit 70 may then be inflated to secure the cannula and laparoscopic instrument together as one movable unit. The inflatable unit 70 may be inflated via, for example, a one-directional valve using a syringe or gas line inserted into a narrow hollow tube 74 connected to the unit 70 as is known in the art. The syringe or gas line may be alternatively inserted directly into a one-directional valve. Thus, means for inflating the unit 70 can be similar to the means for inflating a conventional endotracheal tube. Inflating the inflatable unit 70 also serves to seal the abdomen preventing insufflated gas from escaping through the lumen of the cannula. The inflatable unit 70 then may be deflated, the laparoscopic instrument may be removed, and a different instrument may be inserted.

While the above description of S-shaped instruments 10 and C-shaped cannulas 7 has been directed to procedures performed entirely through the umbilicus, it is to be understood that embodiments of the present invention may be adapted for use in other entry sites. Therefore, when it is desirable to have entry of multiple instruments in a relatively localized area, embodiments of the present invention may be used for such entry, while reducing or eliminating the so-called "chopstick effect". Thus, existing scars or hidden areas such as the pubic hair line or the axillary region may be used as a localized entry site. Procedures such as repair of a ventral hernia may be performed using a non-umbilical localized entry site.

Figure 6:
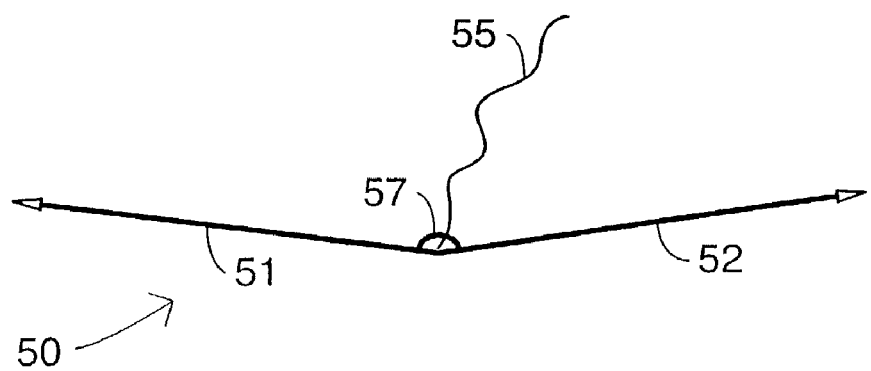
FIG. 6 is a lateral view of an exemplary angulated needle with two sharp ends and a thread attached at the angle of the needle.

As illustrated in FIG. 6, an angulated bidirectional needle 50 in accordance with the present invention is provided with a first sharp end 51, a second sharp end 52, and a surgical thread 55 attached to the angle 57 of the needle 50. The needle 50 has, for example, a total length of around 5-10 cm. The length of each segment from angle to sharp end is roughly equivalent, but need not be. An acute angle of around 160° is formed by the angulated needle 50, however angles 57 ranging from a straight needle, i.e. 180°, to an acute angle 57 of around 90° may be used. The needle is formed out of steel or other suitable material. The surgical thread 55, such as 2-0 nylon, is attached at the angle 57 of the needle 50.

The angulated needle 50 according to an embodiment of the present invention simplifies suture delivery through the gall bladder or other abdominal structure. For example, the first sharp end 51 of the needle 50 is inserted through the body wall by the surgeon. The needle 50 is then grasped within the abdominal cavity 5 by a laparoscopic instrument under endoscopic guidance and is pulled toward the organ of interest. With the second sharp end 52 leading, a stitch is placed through the abdominal structure of interest. The second sharp end 52 is then delivered through the abdominal wall.

The angulated bidirectional needle 50 allows delivery of a stitch without changing the orientation of the sharp end as would be necessary if a needle with only one sharp end is used. Changing orientation of a needle with only one sharp end is a somewhat complicated task requiring advanced laparoscopic skills and may result in iatrogenic injury.

Figure 7:
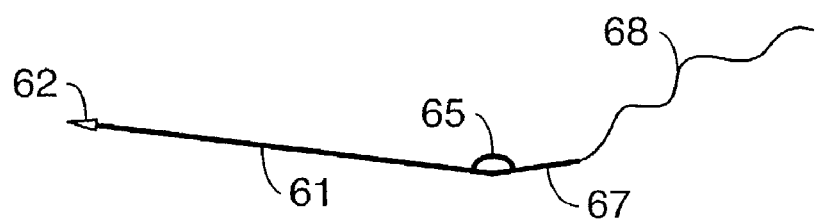
FIG. 7 is a lateral view of an exemplary angulated needle having a long segment with a pointed end on one side of the angle and a short segment having attached thread on the other side of the angle.

An alternative exemplary embodiment of an angulated needle is shown in FIG. 7. In this embodiment the angulated needle 60 has, for example, a long segment 61 with one sharp end 62 on one side of the angle 65. The needle 60 has a blunt short segment 67 on the other side of the angle 65. Thread 68 is attached to the end of the blunt short segment 67.

The angulated needle 60 allows penetration through the body wall as a straight needle. The needle 60 is inserted into and through the wall of the gallbladder. The needle is then flipped 180° and delivered back through the abdominal wall. The angulated needle 60, can be used to reposition a gall bladder or other structure during a laparoscopic procedure by, for example, pulling or relaxing the suture, which eliminates or reduces the need for the insertion of one or more additional cannulas and laparoscopic instruments for that purpose. The angulation of the angulated needle 60 also reduces the chance of iatrogenic injury to surrounding structures by allowing the needle 60 to be flipped and then delivered back through the abdominal wall prior to contacting surrounding abdominal structures.

While several exemplary embodiments of laparoscopic instruments and cannulas for the performance of laparoscopic procedures entirely through the umbilicus have been described herein, it is to be understood that variations may be made in the laparoscopic instruments and cannulas without departing from the spirit and scope of the present invention as defined by the appended claims.

What is claimed is:

1. A laparoscopic surgical method comprising:
   forming an opening in an external skin surface of a patient;
   providing a cannula holder having a perimetric wall and a transverse plate member, said perimetric wall having a longitudinal axis and at least one open end traversed by said axis, said plate member being surrounded by said perimetric wall, said plate member extending generally transversely to said axis, said plate member being spaced from said open end of said perimetric wall, said plate member having a plurality of passageways traversable by respective cannulas, said passageways being spaced from one another;
   inserting said cannula holder through said opening so that said cannula holder is positioned in and traverses said opening;
   disposing a plurality of cannulas in said holder so that said cannulas traverse respective ones of said passageways and are spaced from one another in a plane of said opening and so that after inserting of said holder said cannulas traverse said holder and extend from outside the patient to inside the patient; and
   after inserting of said holder through said opening, inserting a plurality of elongate medical instruments through respective ones of said cannulas.

2. The method defined in claim 1 wherein said holder is deflated or collapsed during the inserting of the cannula holder through said opening, further comprising inflating said holder to an at least partially expanded configuration after inserting of said cannula holder, so that said holder seals said opening.

3. The method defined in claim 2 wherein at least one of said passageways extends from an upper surface of said holder to a lower surface thereof and wherein the disposing of said cannulas in said holder includes passing one of said cannulas through said one of said passageways.

4. The method defined in claim 3, wherein the passing of said one of said cannulas is performed after the inflating of said holder.

5. The method defined in claim 2 wherein the inflating of said holder includes feeding a fluid through a one-way valve into said holder.

6. The method defined in claim 2 wherein the disposing of said cannulas includes coupling at least one of said cannulas to said holder after the inflating of said holder.

7. The method defined in claim 1 wherein the disposing of said cannulas includes coupling at least one of said cannulas to said holder after the inserting of said holder through said opening.

8. The method defined in claim 1 wherein the disposing of said cannulas includes coupling at least one of said cannulas to said holder prior to the inserting of said holder through said opening.

9. The method defined in claim 1 wherein after insertion of one of said instruments through a respective one of said cannulas, said one of said instruments and said respective one of said cannulas have a C-shaped curve in a region traversing said holder.

10. The method defined in claim 1 wherein said opening is formed in an abdominal wall of the patient, said instruments being laparoscopic instruments.

11. A surgical method as defined in claim 1 wherein at least one of said elongate medical instruments has at least one preformed inherently C-shaped section, further comprising:
   inserting said one of said elongate medical instruments through said one of said cannulas so that said C-shaped section at least partially traverses same; and
   bending said one of said cannulas during the inserting of said one of said elongate medical instruments through said one of said cannulas so that said one of said cannulas conforms to the shape of said C-shaped section, said one of said cannulas being flexible and said C-shaped section being sufficiently rigid so that the said one of said cannulas bends to conform to the shape of said C-shaped section.

12. The surgical method defined in claim 11 wherein said C-shaped section is one of two C-shaped sections of said instrument, both of said C-shaped sections being preformed.

13. The surgical method defined in claim 12 wherein said C-shaped sections are disposed in a common plane, face in opposing directions and are at least substantially contiguous with one another, said instrument having an S-shaped form.

14. The surgical method defined in claim 12 wherein said C-shaped sections are substantially rigid.

15. The method defined in claim 1 wherein said cannula holder comprises:
- an upper surface; and
- a lower surface disposed below said upper surface, said plate member defining one of said upper surface and said lower surface; and
- said perimetric wall being connected between said upper surface and said lower surface, a chamber being enclosed within said upper surface, said lower surface and said perimetric wall,
- the disposing of said cannulas including disposing said cannulas through said upper surface and said lower surface, at least one of said cannulas being taken from the group consisting of (i) a flexible cannula and (ii) a curved or arcuate cannula concave on one outer side and convex on an opposite outer side.

16. The surgical method defined in claim 15 wherein at least a given one of said cannulas is spaced from said perimetric wall.

17. The surgical method defined in claim 16 wherein said given one of said cannulas is coupled to said perimetric wall via a connector.

18. The surgical method defined in claim 15 wherein said cannula holder is an inflatable unit.

19. The surgical method defined in claim 15 wherein at least one of said cannulas is disposed within said perimetric wall.

20. The surgical method defined in claim 15 wherein at least one of said cannulas is taken from the group consisting of (i) straight and rigid and (ii) curved and rigid.

21. The surgical method defined in claim 15 wherein at least one of said passageways extends from said upper surface to said lower surface, said one of said passageways being outside said chamber, one of said cannulas being inserted through said one of said passageways.

22. The surgical method defined in claim 15, further comprising an additional cannula disposed outside of said chamber and spaced from said perimetric wall, said additional connector being connected to said cannula holder.

* * * * *

UNITED STATES PATENT AND TRADEMARK OFFICE
CERTIFICATE OF CORRECTION

PATENT NO.       : 7,344,547 B2                                              Page 1 of 1
APPLICATION NO.  : 10/253244
DATED            : March 18, 2008
INVENTOR(S)      : Gregory Piskun It is certified that error appears in the above-identified patent and that said Letters Patent is hereby corrected as shown below:

On the Title Page, Item (73), change the assignee's name from "Phavel Systems, Inc." to -- Pnavel Systems, Inc. --

Signed and Sealed this

Eleventh Day of November, 2008

JON W. DUDAS
*Director of the United States Patent and Trademark Office*